(12) United States Patent
Attersand

(10) Patent No.: US 6,835,556 B2
(45) Date of Patent: Dec. 28, 2004

(54) PROTEIN CLUSTER V

(75) Inventor: Anneli Attersand, Bromma (SE)

(73) Assignee: Pharmacia AB (SE)

( * ) Notice: Subject to any disclaimer, the term of this patent is extended or adjusted under 35 U.S.C. 154(b) by 0 days.

(21) Appl. No.: 10/121,757

(22) Filed: Apr. 12, 2002

(65) Prior Publication Data

US 2003/0104414 A1 Jun. 5, 2003

Related U.S. Application Data

(60) Provisional application No. 60/285,953, filed on Apr. 24, 2001.

(30) Foreign Application Priority Data

Apr. 12, 2001 (SE) .......................................... 0101317-6

(51) Int. Cl.$^7$ ........................... C12P 21/02; C12N 1/21; C12N 15/63
(52) U.S. Cl. ................ 435/69.1; 435/252.3; 435/320.1; 435/325; 536/23.1
(58) Field of Search ............................. 435/69.1, 252.3, 435/320.1, 325, 23.1; 536/23.1; 530/350

(56) References Cited

U.S. PATENT DOCUMENTS 6,100,077 A * 8/2000 Sturley et al. .............. 435/193

FOREIGN PATENT DOCUMENTS

| WO | WO 00017130 | 1/2000 |
|---|---|---|
| WO | WO 00789616 | 12/2000 |

OTHER PUBLICATIONS

Cordes et a. Genome Res. 8 (11), 1097–1108 (1998).*
Velho et al, Diabetes & Metabolism, 23 Suppl. 2:34–37 (1997).
Susulic et al, J. Biol. Chem., 270(49):29483–29492 (1995).
Grujic et al, J. Biol. Chem., 272(28): 17686–17693 (1997).
Goeddel, editor, Methods Enzymol., vol. 185, San Diego; Academic Press, Inc. (1990).
Smith et al, J. Mol. Biol., 147:195–197 (1981).
Pearson, Genomics, 11:635–650 (1991).
Olsen et al, Pac. Symp. Biocomput., 302–313 (1999).
Thompson et al, Nucleic Acid Research, 22:4673–4680 (1994).
Bateman et al, Nucleic Acid Res., 28:263–266 (2000).
Sonhammer et al, Nucleic Acids Research, 26:320–322 (1998).
Sonhammer et al, Proteins, 28:405–420 (197).
Sonhammer et al, ISMB, 6:175–182 (1998).
The C. elegans Sequencing Consortium., Science, 282:2012–2018 (1998).
Published errata appearing in Science , 283:35; 283:2103; and 285:1493 (1999).
Adams et al, Science, 287:2185–2195.
Harrington et al, Curr. Opin. Microbiol., 3(3):285–291 (2000).
Duggan et al, Nature Genetics Supplement, 21:10–14 (1999).
Fields et al, Nature, 340:245–246 (1989).
Chien et al, Proc. Natl. Acad. Sci. U.S.A., 88:9578–9582 (1991).
Bartel et al, Methods in Enzymology, 254:241–263 (1995).
Wallach et al, Curr. Opin. Immunol., 10(2):131–136 (1998).
Hooft van Huijdsduijen, Biotechniques, 24:390–392 (1998).
Lenstra, Cell. Mol. Biol., 41:603–614 (1995).
Rashtchian, Current Opinion in Biotechnology, 6:30–36 (1995).
Fire, Trends in Genetics, 15:358–363 (1999).
Kuwabara et al, Parasitology Today, 16:347–349 (2000).
Fire et al, Nature, 391:806–811 (1998).
Fraser et al, Nature, 408:325–330 (2000).
Gönczy et al, Nature, 408:331–336 (2000).
Lardizabal et al, J. Biol. Chem., 276:38862–38869 (2001).
Cases et al, J. Biol. Chem., 276(42):38870–38876 (2001).
EMBL, Se0101317–6–seq7 (2001).
EMBL, Se0101317–6–seq9 (2001).
EMBL, Se0101317–6–seq17 (2001).
European Bioinformatics Institute Gene Seq. Abstract of WO 00/78961.

* cited by examiner

Primary Examiner—Robert A. Wax

(57) ABSTRACT

The present invention relates to the identification of a human gene family expressed in metabolically relevant tissues. The genes encode a group polypeptides referred to as "Protein Cluster V" which are predicted to be useful in the diagnosis of metabolic diseases, such as obesity and diabetes, as well as in the identification of agents useful in the treatment of the said diseases.

9 Claims, No Drawings

PROTEIN CLUSTER V

This application claims the benefit of U.S. Provisional Application No. 60/285,953, filed Apr. 24, 2001.

TECHNICAL FIELD

The present invention relates to the identification of a human gene family expressed in metabolically relevant tissues. The genes encode a group polypeptides referred to as "Protein Cluster V" which are predicted to be useful in the diagnosis of metabolic diseases, such as obesity and diabetes, as well as in the identification of agents useful in the treatment of the said diseases.

BACKGROUND ART

Metabolic diseases are defined as any of the diseases or disorders that disrupt normal metabolism. They may arise from nutritional deficiencies; in connection with diseases of the endocrine system, the liver, or the kidneys; or as a result of genetic defects. Metabolic diseases are conditions caused by an abnormality in one or more of the chemical reactions essential to producing energy, to regenerating cellular constituents, or to eliminating unneeded products arising from these processes. Depending on which metabolic pathway is involved, a single defective chemical reaction may produce consequences that are narrow, involving a single body function, or broad, affecting many organs and systems.

One of the major hormones that influence metabolism is insulin, which is synthesized in the beta cells of the islets of Langerhans of the pancreas. Insulin primarily regulates the direction of metabolism, shifting many processes toward the storage of substrates and away from their degradation. Insulin acts to increase the transport of glucose and amino acids as well as key minerals such as potassium, magnesium, and phosphate from the blood into cells. It also regulates a variety of enzymatic reactions within the cells, all of which have a common overall direction, namely the synthesis of large molecules from small units. A deficiency in the action of insulin (diabetes mellitus) causes severe impairment in (i) the storage of glucose in the form of glycogen and the oxidation of glucose for energy; (ii) the synthesis and storage of fat from fatty acids and their precursors and the completion of fatty-acid oxidation; and (iii) the synthesis of proteins from amino acids.

There are two varieties of diabetes. Type I is insulin-dependent diabetes mellitus (IDDM), for which insulin injection is required; it was formerly referred to as juvenile onset diabetes. In this type, insulin is not secreted by the pancreas and hence must be taken by injection. Type II, non-insulin-dependent diabetes mellitus (NIDDM) may be controlled by dietary restriction. It derives from insufficient pancreatic insulin secretion and tissue resistance to secreted insulin, which is complicated by subtle changes in the secretion of insulin by the beta cells. Despite their former classifications as juvenile or adult, either type can occur at any age; NIDDM, however, is the most common type, accounting for 90 percent of all diabetes. While the exact causes of diabetes remain obscure, it is evident that NIDDM is linked to heredity and obesity. There is clearly a genetic predisposition to NIDDM diabetes in those who become overweight or obese.

Obesity is usually defined in terms of the body mass index (BMI), i.e. weight (in kilograms) divided by the square of the height (in meters). Weight is regulated with great precision. Regulation of body weight is believed to occur not only in persons of normal weight but also among many obese persons, in whom obesity is attributed to an elevation in the set point around which weight is regulated. The determinants of obesity can be divided into genetic, environmental, and regulatory.

Recent discoveries have helped explain how genes may determine obesity and how they may influence the regulation of body weight. For example, mutations in the of gene have led to massive obesity in mice. Cloning the of gene led to the identification of leptin, a protein coded by this gene; leptin is produced in adipose tissue cells and acts to control body fat. The existence of leptin supports the idea that body weight is regulated, because leptin serves as a signal between adipose tissue and the areas of the brain that control energy metabolism, which influences body weight.

Metabolic diseases like diabetes and obesity are clinically and genetically heterogeneous disorders. Recent advances in molecular genetics have led to the recognition of genes involved in IDDM and in some subtypes of NIDDM, including maturity-onset diabetes of the young (MODY) (Velho & Froguel (1997) Diabetes Metab. 23 Suppl 2:34–37). However, several IDDM susceptibility genes have not yet been identified, and very little is known about genes contributing to common forms of NIDDM. Studies of candidate genes and of genes mapped in animal models of IDDM or NIDDM, as well as whole genome scanning of diabetic families from different populations, should allow the identification of most diabetes susceptibility genes and of the molecular targets for new potential drugs. The identification of genes involved in metabolic disorders will thus contribute to the development of novel predictive and therapeutic approaches.

The $\beta$3-adrenergic receptor (AR) represents one of a number of potential anti-obesity drugs targets for which selective agonists have been developed. In rodents, $\beta$3-AR mRNA is abundant in white adipose tissue (WAT) and brown adipose tissue (BAT). It has been demonstrated that mice lacking endogenous $\beta$3-adrenoreceptors have a slight increase in body fat, but otherwise appear normal (Susulic V. S., et al. (1995) J. Biol. Chem. 270(49). 29483–29492). These-mice are completely resistant to the specific $\beta$3-agonist CL-316,243, which has been shown to increase lipolysis, energy expenditure and affect insulin and leptin levels. When the $\beta$3-AR was ectopically expressed in white and brown adipose tissue or brown adipose tissue only, it was recently demonstrated that the anorectic and insulin secretagogue effects appeared to be mediated by white adipose tissue (Grujic D, et al. (1997) J Biol Chem. 272(28): 17686–93). How these effects are mediated by $\beta$3-AR agonists remains poorly understood.

Lardizabal, K. D. et al. (J. Biol. Chem. 276: 38862–38869) and Cases, S. et al. (J. Biol. Chem. 276: 38870–38876; both papers published Jul. 31, 2001) disclose a new gene family, including members in fungi, plants and animals, which encode proteins corresponding to the "Cluster V" proteins according to the present invention. The proteins were shown to have acyl CoA:diacylglycerol acyltransferase (DGAT; EC 2.3.1.20) function. The gene family is unrelated to the previously identified DGAT(1) family and was designated DGAT2. DGAT2 was shown to have high expression levels in liver and white adipose tissue, suggesting that it may play a significant role in mammalian triglyceride metabolism.

DISCLOSURE OF THE INVENTION

According to the present invention, a family of genes and encoded homologous proteins (hereinafter referred to as "Protein Cluster V") has been identified. Consequently, the present invention provides an isolated nucleic acid molecule selected from:

(a) nucleic acid molecules comprising a nucleotide sequence as shown in SEQ ID NO: 3, 5, 7, 9, 11, 13, 15, 17, or 19.
(b) nucleic acid molecules comprising a nucleotide sequence capable of hybridizing, under stringent hybridization conditions, to a nucleotide sequence complementary to the polypeptide coding region of a nucleic acid molecule as defined in (a); and
(c) nucleic acid molecules comprising a nucleic acid sequence which is degenerate as a result of the genetic code to a nucleotide sequence as defined in (a) or (b).

The nucleic acid molecules according to the present invention includes cDNA, chemically synthesized DNA, DNA isolated by PCR, genomic DNA, and combinations thereof. RNA transcribed from DNA is also encompassed by the present invention.

The term "stringent hybridization conditions" is known in the art from standard protocols (e.g. Ausubel et al., supra) and could be understood as e.g. hybridization to filter-bound DNA in 0.5 M $NaHPO_4$, 7% sodium dodecyl sulfate (SDS), 1 mM EDTA at +65° C., and washing in 0.1×SSC/0.1% SDS at +68° C.

In a preferred form of the invention, the said nucleic acid molecule has a nucleotide sequence identical with SEQ ID NO: 3, 5, 7, 9, 11, 13, 15, 17, or 19 of the Sequence Listing. However, the nucleic acid molecule according to the invention is not to be limited strictly to the sequence shown as SEQ ID NO: 3, 5, 7, 9, 11, 13, 15, 17, or 19. Rather the invention encompasses nucleic acid molecules carrying modifications like substitutions, small deletions, insertions or inversions, which nevertheless encode proteins having substantially the features of the Protein Cluster V polypeptide according to the invention. Included in the invention are consequently nucleic acid molecules, the nucleotide sequence of which is at least 90% homologous, preferably at least 95% homologous, with the nucleotide sequence shown as SEQ ID NO: 3, 5, 7, 9, 11, 13, 15, 17, or 19 in the Sequence Listing.

Included in the invention is also a nucleic acid molecule which nucleotide sequence is degenerate, because of the genetic code, to the nucleotide sequence shown as SEQ ID NO: 3, 5, 7, 9, 11, 13, 15, 17, or 19. A sequential grouping of three nucleotides, a "codon", codes for one amino acid. Since there are 64 possible codons, but only 20 natural amino acids, most amino acids are coded for by more than one codon. This natural "degeneracy", or "redundancy", of the genetic code is well known in the art. It will thus be appreciated that the nucleotide sequence shown in the Sequence Listing is only an example within a large but definite group of sequences which will encode the Protein Cluster V polypeptide.

The nucleic acid molecules according to the invention have numerous applications in techniques known to those skilled in the art of molecular biology. These techniques include their use as hybridization probes, for chromosome and gene mapping, in PCR technologies, in the production of sense or antisense nucleic acids, in screening for new therapeutic molecules, etc.

More specifically, the sequence information provided by the invention makes possible large-scale expression of the encoded polypeptides by techniques well known in the art. Nucleic acid molecules of the invention also permit identification and isolation of nucleic acid molecules encoding related polypeptides, such as human allelic variants and species homologues, by well-known techniques including Southern and/or Northern hybridization, and PCR. Knowledge of the sequence of a human DNA also makes possible, through use of Southern hybridization or PCR, the identification of genomic DNA sequences encoding the proteins in Cluster V, expression control regulatory sequences such as promoters, operators, enhancers, repressors, and the like. Nucleic acid molecules of the invention are also useful in hybridization assays to detect the capacity of cells to express the proteins in Cluster V. Nucleic acid molecules of the invention may also provide a basis for diagnostic methods useful for identifying a genetic alteration(s) in a locus that underlies a disease state or states, which information is useful both for diagnosis and for selection of therapeutic strategies.

In a further aspect, the invention provides an isolated polypeptide encoded by the nucleic acid molecule as defined above. In a preferred form, the said polypeptide has an amino acid sequence according to SEQ ID NO: 4, 6, 8, 10, 12, 14, 16, 18 or 20 of the Sequence Listing. However, the polypeptide according to the invention is not to be limited strictly to a polypeptide with an amino acid sequence identical with SEQ ID NO: 4, 6, 8, 10, 12, 14, 16, 18 or 20 in the Sequence Listing. Rather the invention encompasses polypeptides carrying modifications like substitutions, small deletions, insertions or inversions, which polypeptides nevertheless have substantially the features of the Protein Cluster V polypeptide. Included in the invention are consequently polypeptides, the amino acid sequence of which is at least 90% homologous, preferably at least 95% homologous, with the amino acid sequence shown as SEQ ID NO: 4, 6, 8, 10, 12, 14, 16, 18 or 20 in the Sequence Listing.

In a further aspect, the invention provides a vector harboring the nucleic acid molecule as defined above. The said vector can e.g. be a replicable expression vector, which carries and is capable of mediating the expression of a DNA molecule according to the invention. In the present context the term "replicable" means that the vector is able to replicate in a given type of host cell into which is has been introduced. Examples of vectors are viruses such as bacteriophages, cosmids, plasmids and other recombination vectors. Nucleic acid molecules are inserted into vector genomes by methods well known in the art.

Included in the invention is also a cultured host cell harboring a vector according to the invention. Such a host cell can be a prokaryotic cell, a unicellular eukaryotic cell or a cell derived from a multicellular organism. The host cell can thus e.g. be a bacterial cell such as an *E. coli* cell; a cell from yeast such as *Saccharomyces cervisiae* or *Pichia pastoris*, or a mammalian cell. The methods employed to effect introduction of the vector into the host cell are standard methods well known to a person familiar with recombinant DNA methods.

In yet another aspect, the invention provides a process for production of a polypeptide, comprising culturing a host cell, according to the invention, under conditions whereby said polypeptide is produced, and recovering said polypeptide. The medium used to grow the cells may be any conventional medium suitable for the purpose. A suitable vector may be any of the vectors described above, and an appropriate host cell may be any of the cell types listed above. The methods employed to construct the vector and effect introduction thereof into the host cell may be any methods known for such purposes within the field of recombinant DNA. The recombinant polypeptide expressed by the cells may be secreted, i.e. exported through the cell membrane, dependent on the type of cell and the composition of the vector.

In a further aspect, the invention provides a method for identifying an agent capable of modulating a nucleic acid molecule according to the invention, comprising
(i) providing a cell comprising the said nucleic acid molecule;
(ii) contacting said cell with a candidate agent; and
(iii) monitoring said cell for an effect that is not present in the absence of said candidate agent.

For screening purposes, appropriate host cells can be transformed with a vector having a reporter gene under the control of the nucleic acid molecule according to this invention. The expression of the reporter gene can be measured in the presence or absence of an agent with known activity (i.e. a standard agent) or putative activity (i.e. a "test agent" or "candidate agent"). A change in the level of expression of the reporter gene in the presence of the test agent is compared with that effected by the standard agent. In this way, active agents are identified and their relative potency in this assay determined.

A transfection assay can be a particularly useful screening assay for identifying an effective agent. In a transfection assay, a nucleic acid containing a gene such as a reporter gene that is operably linked to a nucleic acid molecule according to the invention, is transfected into the desired cell type. A test level of reporter gene expression is assayed in the presence of a candidate agent and compared to a control level of expression. An effective agent is identified as an agent that results in a test level of expression that is different than a control level of reporter gene expression, which is the level of expression determined in the absence of the agent. Methods for transfecting cells and a variety of convenient reporter genes are well known in the art (see, for example, Goeddel (ed.), Methods Enzymol., Vol. 185, San Diego: Academic Press, Inc. (1990); see also Sambrook, supra).

Throughout this description the terms "standard protocols" and "standard procedures", when used in the context of molecular biology techniques, are to be understood as protocols and procedures found in an ordinary laboratory manual such as: Current Protocols in Molecular Biology, editors F. Ausubel et al., John Wiley and Sons, Inc. 1994, or Sambrook, J., Fritsch, E. F. and Maniatis, T., Molecular Cloning: A laboratory manual, 2nd Ed., Cold Spring Harbor Laboratory Press, Cold Spring Harbor, N.Y. 1989.

EXAMPLES

Example 1
Identification of Protein Clusters

A family of homologous proteins (hereinafter referred to as "Protein Cluster V") was identified by an "all-versus-all" BLAST procedure using all *Caenorhabditis* elegans proteins in the Wormpep20 database release (sanger.ac.uk/Projects/ C. elegans/wormpep/index.shtml). The Wormpep database contains the predicted proteins from the *C. elegans* genome sequencing project, carried out jointly by the Sanger Centre in Cambridge, UK and the Genome Sequencing Center in St. Louis, USA. A number of 18,940 proteins were retrieved from Wormpep20. The proteins were used in a Smith-Waterman clustering procedure to group together proteins of similarity (Smith T. F. & Waterman M. 5. (1981) Identification of common molecular subsequences. J. Mol. Biol. 147(1): 195–197; Pearson W R. (1991) Searching protein sequence libraries: comparison of the sensitivity and selectivity of the Smith-Waterman and FASTA algorithms. Genomics 11: 63 5–650; Olsen et al. (1999) Optimizing Smith-Waterman alignments. Pac Symp Biocomput. 302–313). Completely annotated proteins were filtered out, whereby 10,130 proteins of unknown function could be grouped into 1,800 clusters.

The obtained sequence clusters were compared to the Drosophila melanogaster proteins contained in the database Flybase (Berkeley Drosophila Genome Project; fruitfly.org), and annotated clusters were removed. Non-annotated protein clusters, conserved in both *C. elegans* and *D. melanogaster*, were saved to a worm/fly data set, which was used in a BLAST procedure (ncbi.nlm.nih.gov/Education/ BLASTinfo/information3.html) against the Celera Human Genome Database (http://www.celera.com) (celera.com. Overlapping fragments were assembled to, as close as possible, full-length proteins using the PHRAP software, developed at the University of Washington (genome.washington.edu/UWGC/analysistools/phrap.htm). A group of homologous proteins ("Protein Cluster V") with unknown function was chosen for further studies.

EST databases provided by the EMBL (embl.org/ Services/index.html) were used to check whether the human proteins in Cluster V were expressed, in order to identify putative pseudogenes. One putative pseudogene was identified and excluded.

Example 2
Analyses of Protein Cluster V
(a) Alignment

The human part of this protein family includes seven different 150–250 residue polypeptides shown as SEQ ID NO: 2, 4, 6, 8, 10, 12, 14, 16, 18 and 20, encoded by the nucleic acid sequences shown as SEQ ID NO: 1, 3, 5, 7, 9, 11, 13, 15, 17, and 19. The amino acid sequence shown as SEQ ID NO: 2 was identified to correspond to a human 261 aa sequence encoded by the gene "WUGSC: H_DJ0747G18.5" (GenBank Accession No. AC004876). No function has been associated with the said gene.

An alignment of the human polypeptides included in Protein Cluster V, using the ClustalW multiple alignment software (Thompson et al. (1994) Nucleic Acid Research 22: 4673–4680) is shown in Table I. The alignment showed a high degree of conservation over a 100 residues region in the protein (corresponding to positions 23–147 in SEQ ID NO: 2), indicating the presence of a novel domain.

(b) HMM-Pfam

A HMM-Pfam search was performed on the human family members. Pfam is a large collection of protein families and domains. Pfam contains multiple protein alignments and profile-HMMs (Profile Hidden Markov Models) of these families. Profile-HMMs can be used to do sensitive database searching using statistical descriptions of a sequence family's consensus. Pfam is available on the WWW at pfam.wustl.edu, sanger.ac.uk/Software/Pfam; and cgr.ki.se/Pfam. The latest version (4.3) of Pfam contains 1815 families. These Pfam families match 63% of proteins in SWISS-PROT 37 and TrEMBL 9. For references to Pfam, see Bateman et al. (2000) The Pfam protein families database. Nucleic Acids Res. 28:263–266; Sonnhammer et al. (1998) Pfam: Multiple Sequence Alignments and HMM-Profiles of Protein Domains. Nucleic Acids Research, 26:322–325; Sonnhammer et al. (1997) Pfam: a Comprehensive Database of Protein Domain Families Based on Seed Alignments. Proteins 28:405–420.

The HMM-Pfam search indicated that no previously known domains could be identified in Protein Cluster V.

(c) TM-HMM

The human proteins in Cluster V were analyzed using the TM-HMM tool available e.g. at http://www.cbs.dtu.dk/ services/TMHMM-1.0. TM-HMM is a method to model and predict the location and orientation of alpha helices in membrane-spanning proteins (Sonnhammer et al. (1998) *A hidden Markov model for predicting transmembrane helices*

*in protein sequences.* ISMB 6:175–182). The results indicate that the human Cluster V proteins contain 3–4 transmembrane segments.

(d) Analysis of Non-Human Orthologs

The *Caenorhabditis elegans* genome includes four genes, designated K07B1.4 (GenBank Accession No. AF003384), F59A1.10 (GenBank Accession No. Z81557), Y53G8B.2 (GenBank Accession No. AC006804), and W01A11.2 (GenBank Accession No. U64852) orthologous to the human Cluster V genes. The closest ancestor (K07B1.4) is on average 44% identical to the 10 human gene products. (See also: *Genome sequence of the nematode C. elegans: a platform for investigating biology*; The *C. elegans* Sequencing Consortium. Science (1998) 282:2012–2018. Published errata appear in Science (1999) 283:35; 283:2103; and 285:1493.)

The *Drosophila melanogaster* genome includes four genes orthologous to human Cluster V. The most closely related genes, designated "CG1942" (GenBank Accession No. AE003840_36) and gene: "CG1946" (GenBank Accession No. AE003840_37) are 39% identical to the human gene products. (See also Adams et al. (2000) *The genome sequence of Drosophila melanogaster*; Science 287:2185–2195) is 42% identical to the human protein set.

The human proteins in Cluster V show 27% identity to two yeast proteins; *S. Cerevisiae* SCYOR245C_1 (GenBank Accession No. Z75153) and *S. pombe* SPCC548_1 (GenBank Accession No. AL359685). The yeast proteins are of unknown function.

Example 3

Expression Analysis

The tissue distribution of the human genes was studied using the Incyte LIFESEQ® database incite.com. The genes shown as SEQ ID NO: 1, 3, 5, 7, 9, 11, 13, 15, 17 were found to be expressed primarily in the following tissues:
SEQ ID NO: 1 and 3: Liver, digestive system
SEQ ID NO: 7 and 9: Exocrine Glands, Connective Tissue, Germ Cells
SEQ ID NO: 11: Female genitalia, urinary tract
SEQ ID NO: 17: Female genitalia, nervous system
SEQ ID NO: 13 and 15: Digestive System
SEQ ID NO: 5: Cardiovascular system Therefore, the said nucleic acid molecules and the encoded polypeptides shown are proposed to be useful for differential identification of the tissues or cell types present in a biological sample and for diagnosis of diseases and disorders related to the tissues where the genes are expressed.

Example 4

Effect of β3-AR Agonists on Cluster V Genes.

Microarrays consist of a highly ordered matrix of thousands of different DNA sequences that can be used to measure DNA and RNA variation in applications that include gene expression profiling, comparative genomics and genotyping (For recent reviews, see e.g.: Harrington et al. (2000) *Monitoring gene expression using DNA microarrays*. Curr. Opin. Microbiol. 3(3): 285–291; or Duggan et al. (1999) *Expression profiling using cDNA Microarrays*. Nature Genetics Supplement 21:10–14).

In order to investigate the mechanisms whereby β3-AR agonists affect gene regulation in adipose tissue in vivo, a study was carried out using Affymetrix GENECHIP® oligonucleotide arrays by comparing the transcript profiles of a large number of genes in white adipose tissue derived from C57BL/6J mice treated with the β3-AR agonist CL-316, 243, or from control mice injected with a saline solution.

PolyA$^+$ mRNAs were extracted from white adipose tissue from control and β3-AR agonist treated mice respectively. They were reverse transcribed using a T7-tagged oligo-dT primer and double-stranded cDNAs were generated. These cDNAs were then amplified and labeled using In Vitro Transcription (IVT) with T7 RNA polymerase and biotinylated nucleotides. The populations of cRNAs obtained after IVT were purified and fragmented by heat to produce a distribution of RNA fragment sizes from approximately 35 to 200 bases. Two Affymetrix Mu 19K and Mu11K sets of 3 arrays (subA, subB and subC) and 2 arrays (subA and subB) respectively, were hybridized (using the recommended buffer) overnight at 45° C. with the control or the treated denatured samples. The arrays were then washed and stained with R-phycoerythrin streptavidin with the help of an Affymetrix fluidics station. The cartridges were scanned using a Hewlett-Packard confocal scanner and the images were analyzed with the GeneChip 3.1 software (Affymetrix).

The results indicate that the mouse gene (GenBank accession No. AA275948), orthologous to the worm gene F59A1.10, is down-regulated by β3-AR agonist treatment. It is hypothesized that the human genes in Cluster V are similarly involved in metabolically important signaling pathways.

Example 5

Multiple Tissue Northern Blotting

Multiple Tissue Northern blotting (MTN) is performed to make a more thorough analysis of the expression profiles of the proteins in Cluster V. Multiple Tissue Northern (MTN™) Blots (clontech.com/mtn) are pre-made Northern blots featuring Premium Poly A+RNA from a variety of different human, mouse, or rat tissues. MTN Blots can be used to analyze size and relative abundance of transcripts in different tissues. MTN Blots can also be used to investigate gene families and alternate splice forms and to assess cross species homology.

Example 6

Identification of Polypeptides Binding to Protein Cluster V

In order to assay for proteins interacting with Protein Cluster V, the two-hybrid screening method can be used. The two-hybrid method, first described by Fields & Song (1989) Nature 340:245–247, is a yeast-based genetic assay to detect protein-protein interactions in vivo. The method enables not only identification of interacting proteins, but also results in the immediate availability of the cloned genes for these proteins.

The two-hybrid method can be used to determine if two known proteins (i.e. proteins for which the corresponding genes have been previously cloned) interact. Another important application of the two-hybrid method is to identify previously unknown proteins that interact with a target protein by screening a two-hybrid library. For reviews, see e.g.: Chien et al. (1991) The two-hybrid system: a method to identify and clone genes for proteins that interact with a protein of interest. Proc. Natl. Acad. Sci. U.S.A. 88:9578–9582; Bartel P L, Fields (1995) Analyzing protein-protein interactions using two-hybrid system. Methods Enzymol. 254:241–263; or Wallach et al. (1998) The yeast two-hybrid screening technique and its use in the study of protein-protein interactions in apoptosis. Curr. Opin. Immunol. 10(2): 131–136. See also clontech.com/matchmaker.

The two-hybrid method uses the restoration of transcriptional activation to indicate the interaction between two proteins. Central to this technique is the fact that many eukaryotic transcriptional activators consist of two physically discrete modular domains: the DNA-binding domain (DNA-BD) that binds to a specific promoter sequence and the activation domain (AD) that directs the RNA polymerase II complex to transcribe the gene downstream of the DNA binding site. The DNA-BD vector is used to generate a fusion of the DNA-BD and a bait protein X, and the AD vector is used to generate a fusion of the AD and another protein Y. An entire library of hybrids with the AD can also be constructed to search for new or unknown proteins that interact with the bait protein. When interaction occurs between the bait protein X and a candidate protein Y, the two functional domains, responsible for DNA binding and activation, are tethered, resulting in functional restoration of transcriptional activation. The two hybrids are cotransformed into a yeast host strain harboring reporter genes containing appropriate upstream binding sites; expression of the reporter genes then indicates interaction between a candidate protein and the target protein.

Example 7

Full-length Cloning of Cluster V Genes

The polymerase chain reaction (PCR), which is a well-known procedure for in vitro enzymatic amplification of a specific DNA segment, can be used for direct cloning of Protein Cluster V genes. Tissue cDNA can be amplified by PCR and cloned into an appropriate plasmid and sequenced. For reviews, see e.g. Hooft van Huijsduijnen (1998) *PCR-assisted cDNA cloning: a guided tour of the minefield.* Biotechniques 24:390–392; Lenstra (1995) *The applications of the polymerase chain reaction in the life sciences.* Cellular & Molecular Biology 41:603–614; or Rashtchian (1995) *Novel methods for cloning and engineering genes using the polymerase chain reaction.* Current Opinion in Biotechnology 6:30–36. Various methods for generating suitable ends to facilitate the direct cloning of PCR products are given e.g. in Ausubel et al. supra (section 15.7).

In an alternative approach to isolate a cDNA clone encoding a full length protein of Protein Cluster V, a DNA fragment corresponding to a nucleotide sequence selected from the group consisting of SEQ ID NO: 1, 3, 5, 7, 9, 11, 13, 15, 17 or 19, or a portion thereof, can be used as a probe for hybridization screening of a phage cDNA library. The DNA fragment is amplified by the polymerase chain reaction (PCR) method. The primers are preferably 10 to 25 nucleotides in length and are determined by procedures well known to those skilled in the art. A lambda phage library containing cDNAs cloned into lambda phage-vectors is plated on agar plates with *E. coli* host cells, and grown. Phage plaques are transferred to nylon membranes, which are hybridized with a DNA probe prepared as described above. Positive colonies are isolated from the plates. Plasmids containing cDNA are rescued from the isolated phages by standard methods. Plasmid DNA is isolated from the clones. The size of the insert is determined by digesting the plasmid with appropriate restriction enzymes. The sequence of the entire insert is determined by automated sequencing of the plasmids.

Example 8

Recombinant Expression of Proteins in Eukaryotic Host Cells

To produce proteins of Cluster V, a polypeptide-encoding nucleic acid molecule is expressed in a suitable host cell using a suitable expression vector and standard genetic engineering techniques. For example, the polypeptide-encoding sequence is subcloned into a commercial expression vector and transfected into mammalian, e.g. Chinese Hamster Ovary (CHO), cells using a standard transfection reagent. Cells stably expressing a protein are selected. Optionally, the protein may be purified from the cells using standard chromatographic techniques. To facilitate purification, antisera is raised against one or more synthetic peptide sequences that correspond to portions of the amino acid sequence, and the antisera is used to affinity purify the protein.

Example 9

Determination of Gene Function

Methods are known in the art for elucidating the biological function or mode of action of individual genes. For instance, RNA interference (RNAi) offers a way of specifically and potently inactivating a cloned gene, and is proving a powerful tool for investigating gene function. For reviews, see e.g. Fire (1999) *RNA-triggered gene silencing*. Trends in Genetics 15:358–363; or Kuwabara & Coulson (2000) *RNAi-prospects for a general technique for determining gene function*. Parasitology Today 16:347–349. When double-stranded RNA (dsRNA) corresponding to a sense and antisense sequence of an endogenous mRNA is introduced into a cell, the cognate mRNA is degraded and the gene is silenced. This type of posttranscriptional gene silencing (PTGS) was first discovered in *C. elegans* (Fire et al., (1998) Nature 391:806–81 1). RNA interference has recently been used for targeting nearly 90% of predicted genes on *C. elegans* chromosome I (Fraser et al. (2000) Nature 408: 325–330) and 96% of predicted genes on *C. elegans* chromosome III (Gönczy et al. (2000) Nature 408:331–336).

TABLE I

| Alignment of polypeptides in Protein Cluster V | | |
|---|---|---|
| SEQ_2 | ------------------------------------------------------------ | |
| SEQ_4 | ------------------------------------------------------------ | |
| SEQ_8 | ------------------------------------------------------------ | |
| SEQ_10 | ------------------------------------------------------------ | |
| SEQ_12 | ------------------------------------------------------------ | |
| SEQ_14 | ------------------------------------------------------------ | |
| SEQ_20 | MVNGKSITSLQSNKNLAAIHGPKYLCGNFGPRWQAFSLGTKLDPMEVFPKLLPSKVPVAQ | 60 |
| SEQ_16 | ------------------------------------------------------------ | |

TABLE I-continued
Alignment of polypeptides in Protein Cluster V

```
SEQ_18  ------------------------------------------------------------
SEQ_6   ------------------------------------------------------------
SEQ_2   ------------------------------------------------------------
SEQ_4   ------------------------------------------------------------
SEQ_8   ------------------------------------------------------------
SEQ_10  ------------------------------------------------------------
SEQ_12  ------------------------------------------------------------
SEQ_14  ------------------------------------------------------------
SEQ_20  TLAPYSAPCFQRLWWSAAKVKAPSHNAKQGPKMDGQLVKTHDLSPKHNYIIANHPHGILS  120
SEQ_16  -----------------------------------------------------RPGGSEG    7
SEQ_18  ------------------------------------------------------------
SEQ_6   ------------------------------------------------------------
SEQ_2   -------EAPLFSRCLAFHPPFILLNTPKLVKTAELPPDRNYVLGAHPHGIMCTGFLCNF   53
SEQ_4   LGTLLGWRAPLFSRCLAFHPPFILLNTPKLVKTAELPPDRNYVLGAHPHGIMCTGFLCNF   60
SEQ_8   --AFCNFSTEATEVSKKFPGIRPYLATLAGNFRMPVLREYLMSGGICPVSRDTIDYLLSK   58
SEQ_10  ------------------------------------------------------------
SEQ_12  ------------------------------------------------------------
SEQ_14  ---------------------------------------------------------NLF    3
SEQ_20  FGVFINFATEATGIARIFPSITPFVGTLERIFWIPIVREYVMSMGVCPVSSSALKYLLTQ  180
SEQ_16  RFPKVTPVSGRVRAGTQAPPWLSRLPSLQLVKTAELDPSRNYIAGFHPHGVLAVGAFANL   67
SEQ_18  ---------------------SDYVPLKLLKTHDICPSRNYILVCHPGLFAHGWFGHF    38
SEQ_6   -------------------------CSEIFASLRLPR---IMAHSKQPSHFQSLMLLQW   31
SEQ_2   STESHGFSQLFPGLRPWLSVLAG-----LFYLPVYRDYIMSFGLCPVSRQSLD----FIL  104
SEQ_4   STESNGFSQLFPGLRPWLAVLAG-----LFYLPVYRDYIMSFGASLVPVYSFGENDIFRL  115
SEQ_8   NGSGNAIIIVVGGAAESLSSMPGKNAVTLRNRKGFVKLALRHGADLVPIYSFGENEVYKQ  118
SEQ_10  --------------------------RNRKGFVKLALRHGADLVPIYSFGENEVYKQ    31
SEQ_12  --------------KESLDAHPGKFTLFIRQRKGFVKIALTHGASLVPVVSFGENELFKQ   46
SEQ_14  EAHKLKFNIIVGGAQEALDARPGSFTLLLRNRKGFVRLALTHGAPLVXIFSFGENDLFDQ   63
SEQ_20  KGSGNAVVIVVGGAAEALLCRPGASTLFLKQRKGFVKMALQTGAYLVPSYSFGENEVFNQ  240
SEQ_16  CTESTGFSSIFPGIRPHLMMLTL-----WFRAPFFRDYIMSAGLVTSEKESAAHILNRKG  122
SEQ_18  ATEASGFSKIFPGITPYILTLGA-----FFWMPFLREYVMSTGACSVSRSSIDFLLTHKG   93
SEQ_6   PLSYLAIFWILQPLFVYLLFTSLWPLPVLYFAWLFLDWKTPERGGRRSAWVRNWCVWTHI   91
SEQ_2   SQPQLG-------QAVVI----MVGGAEALYSVPGEHCLTLQKRKGFVRLALRHGASLVP  153
SEQ_4   KAFATGSWQHWCQLTFKK----LMGFSPCIFWGRGLFSATSWGLLPFAVPITTVVGRPIP  171
SEQ_8   VIFEEGSWGRWVQKKFQ----KYIGFAPCIFHGRGLFSSDTWGLVPYSKPITTVVGEPIT  174
SEQ_10  VIFEEGSWGRWVQKKFQ----KYIGFAPCIFHGRGLFSSDTWGLVPYSKPITTVGGGKIQ   87
SEQ_12  TDNPEGSWIRTVQNKLQ----KIMGFALPLFHARGVFQYN-FGLMTYRKAIHTVVGRPIP  101
SEQ_14  IPNSSGSWLRYIQNRLQ----KIMG----------------------------------   84
```

TABLE I-continued

Alignment of polypeptides in Protein Cluster V

```
SEQ_20  ETFPEGTWLRLFQKTFQDTFKKILGLNFCTFHGRG-FTRGSWGFLPFNRPITTVVGEPLP  299

SEQ_16  GGNLLGIIVG--------------GAQEALDARPGSFTLLLRNRKGFVRLALTHG-----  163

SEQ_18  TGNMVIVVIG--------------GLAECRYSLPGSSTLVLKNRSGFVRMALQHGVPLIP  139

SEQ_6   RDYFPITILK------------TKDLSPEHNYLMGVHPMGLLTFGAFCNFC---------  130

SEQ_2   VYS---FGENDIFRLKAFATGSWQHWCQLTFKKL-MGFSPCIFWVAV              196

SEQ_4   VPQRLHPTEEEVNHYHALYMTDLEQLFEEHKESCGVPASTCLTFI--              216

SEQ_8   IPKLEHPTQQDIDLYHTMYMEALVKLFDKHKTKFGLPETEVLEVN--              219

SEQ_10  S----RSKKRKINXX-------------QNDSCYSL-----------              106

SEQ_12  VRQTLNPTQEQIEELHQTYMEELRKLFEEHKGKYGIPEHETLVLK--              146

SEQ_14  ----------------------------------------------

SEQ_20  IPRIKRPNQKTVDKYHALYISALRKLFDQHKVEYGLPETQELTIT--              344

SEQ_16  ----------------------------------------------

SEQ_18  AYAFGETDL-------------------------------------              148

SEQ_6   ----------------------------------------------
```

---

What is claimed is:

1. An isolated nucleic acid molecule selected from the group consisting of:
   (a) nucleic acid molecules consisting of a nucleotide sequence as shown in SEQ ID NO: 3, 5, 7, 9, 11, 13, 15, 17 or 19, or a nucleotide sequence which is at least 90% homologous with a nucleotide sequence as shown in SEQ ID NO: 3, 5, 7, 9, 11, 13, 15, 17 or 19;
   (b) nucleic acid molecules consisting of a nucleotide sequence capable of hybridizing, along its full length, under stringent hybridization conditions, to a nucleotide sequence complementary to the polypeptide coding region of a nucleic acid molecule as defined in (a); and
   (c) nucleic acid molecules consisting of a nucleic acid sequence which is degenerate as a result of the genetic code to a nucleotide sequence as defined in (a) or (b).

2. A vector harboring the nucleic acid molecule according to claim 1.

3. A replicable expression vector which carries and is capable of mediating the expression of a nucleotide sequence according to claim 1.

4. A cultured host cell harboring a vector according to claim 2.

5. A process for production of a polypeptide, comprising culturing a host cell according to claim 4 under conditions whereby said polypeptide is produced, and recovering said polypeptide.

6. A cultured host cell harboring a vector according to claim 3.

7. A process for production of a polypeptide, comprising culturing a host cell according to claim 6 under conditions whereby said polypeptide is produced, and recovering said polypeptide.

8. An isolated nucleic acid molecule according to claim 1, selected from the group consisting of nucleic acid molecules consisting of a nucleotide sequence as shown in SEQ ID NO: 3, 5, 7, 9, 11, 13, 15, 17 or 19, or a nucleotide sequence which is at least 90% homologous with a nucleotide sequence as shown in SEQ ID NO: 3, 5, 7, 9, 11, 13, 15, 17 or 19.

9. An isolated nucleic acid molecule according to claim 1, selected from the group consisting of nucleic acid molecules consisting of a nucleotide sequence as shown in SEQ ID NO: 3, 5, 7, 9, 11, 13, 15, 17 or 19.

* * * * *

SEQUENCE LISTING

<160> NUMBER OF SEQ ID NOS: 20

<210> SEQ ID NO 1
<211> LENGTH: 593
<212> TYPE: DNA
<213> ORGANISM: human
<220> FEATURE:
<221> NAME/KEY: CDS
<222> LOCATION: (3)..(593)
<223> OTHER INFORMATION:

<400> SEQUENCE: 1

```
tg gag gcc cct ctt ttc agc cgg tgt ctt gcc ttc cat cct ccc ttc      47
   Glu Ala Pro Leu Phe Ser Arg Cys Leu Ala Phe His Pro Pro Phe
    1               5                  10                  15 atc ctg ctc aac acc ccg aag ctg gtg aaa aca gca gag ctg ccc ccg     95
Ile Leu Leu Asn Thr Pro Lys Leu Val Lys Thr Ala Glu Leu Pro Pro
             20                  25                  30 gat cgg aac tac gtg ctg ggc gcc cac cct cat ggg atc atg tgt aca    143
Asp Arg Asn Tyr Val Leu Gly Ala His Pro His Gly Ile Met Cys Thr
         35                  40                  45 ggc ttc ctc tgt aat ttc tcc acc gag agc cat ggc ttc tcc cag ctc    191
Gly Phe Leu Cys Asn Phe Ser Thr Glu Ser His Gly Phe Ser Gln Leu
     50                  55                  60 ttc ccg ggg ctc cgg ccc tgg tta tcc gtg ctg gct ggc ctc ttc tac    239
Phe Pro Gly Leu Arg Pro Trp Leu Ser Val Leu Ala Gly Leu Phe Tyr
 65                  70                  75 ctc ccg gtc tat cgc gac tac atc atg tcc ttt gga ctc tgt ccg gtg    287
Leu Pro Val Tyr Arg Asp Tyr Ile Met Ser Phe Gly Leu Cys Pro Val
 80                  85                  90                  95 agc cgc cag agc ctg gac ttc atc ctg tcc cag ccc cag ctc ggg cag    335
Ser Arg Gln Ser Leu Asp Phe Ile Leu Ser Gln Pro Gln Leu Gly Gln
             100                 105                 110
```

-continued

| | |
|---|---|
| gcc gtg gtc atc atg gtg ggg ggt gcg cac gag gcc ctg tat tca gtc<br>Ala Val Val Ile Met Val Gly Gly Ala His Glu Ala Leu Tyr Ser Val<br>115                          120                     125 | 383 |
| ccc ggg gag cac tgc ctt acg ctc cag aag cgc aaa ggc ttc gtg cgc<br>Pro Gly Glu His Cys Leu Thr Leu Gln Lys Arg Lys Gly Phe Val Arg<br>    130                       135                   140 | 431 |
| ctg gcg ctg agg cac ggg gcg tcc ctg gtg ccc gtg tac tcc ttt ggg<br>Leu Ala Leu Arg His Gly Ala Ser Leu Val Pro Val Tyr Ser Phe Gly<br>145                         150                   155 | 479 |
| gag aat gac atc ttt aga ctt aag gct ttt gcc aca ggc tcc tgg cag<br>Glu Asn Asp Ile Phe Arg Leu Lys Ala Phe Ala Thr Gly Ser Trp Gln<br>160                   165               170               175 | 527 |
| cat tgg tgc cag ctc acc ttc aag aag ctc atg ggc ttc tct cct tgc<br>His Trp Cys Gln Leu Thr Phe Lys Lys Leu Met Gly Phe Ser Pro Cys<br>        180                 185               190 | 575 |
| atc ttc tgg gtc gcg gtc<br>Ile Phe Trp Val Ala Val<br>             195 | 593 |

<210> SEQ ID NO 2
<211> LENGTH: 197
<212> TYPE: PRT
<213> ORGANISM: human

<400> SEQUENCE: 2

Glu Ala Pro Leu Phe Ser Arg Cys Leu Ala Phe His Pro Pro Phe Ile
1                5                    10                  15

Leu Leu Asn Thr Pro Lys Leu Val Lys Thr Ala Glu Leu Pro Pro Asp
              20                    25                   30

Arg Asn Tyr Val Leu Gly Ala His Pro His Gly Ile Met Cys Thr Gly
           35                    40                   45

Phe Leu Cys Asn Phe Ser Thr Glu Ser His Gly Phe Ser Gln Leu Phe
    50                     55                   60

Pro Gly Leu Arg Pro Trp Leu Ser Val Leu Ala Gly Leu Phe Tyr Leu
65               70                  75                  80

Pro Val Tyr Arg Asp Tyr Ile Met Ser Phe Gly Leu Cys Pro Val Ser
           85                    90                   95

Arg Gln Ser Leu Asp Phe Ile Leu Ser Gln Pro Gln Leu Gly Gln Ala
             100                  105                110

Val Val Ile Met Val Gly Gly Ala His Glu Ala Leu Tyr Ser Val Pro
        115                    120                  125

Gly Glu His Cys Leu Thr Leu Gln Lys Arg Lys Gly Phe Val Arg Leu
130                   135                140

Ala Leu Arg His Gly Ala Ser Leu Val Pro Val Tyr Ser Phe Gly Glu
145               150               155                 160

Asn Asp Ile Phe Arg Leu Lys Ala Phe Ala Thr Gly Ser Trp Gln His
               165                   170               175

Trp Cys Gln Leu Thr Phe Lys Lys Leu Met Gly Phe Ser Pro Cys Ile
        180                   185                190

Phe Trp Val Ala Val
        195

<210> SEQ ID NO 3
<211> LENGTH: 822
<212> TYPE: DNA
<213> ORGANISM: human
<220> FEATURE:
<221> NAME/KEY: CDS
<222> LOCATION: (93)..(740)

<223> OTHER INFORMATION:

<400> SEQUENCE: 3

```
aaaaaaaaac ctgggccctt aaccctatcc taagaacctt taactcggaa ctctgctggg        60 gtggccttg acccta tcct aagaacctttaa ctc gga act ctg ttg ggg tgg          113
                                     Leu Gly Thr Leu Leu Gly Trp
                                       1               5 agg gcc cct ctt ttc agc cgg tgt ctt gcc ttc cat cct ccc ttc atc        161
Arg Ala Pro Leu Phe Ser Arg Cys Leu Ala Phe His Pro Pro Phe Ile
         10                  15                  20 ctg ctc aac acc ccg aag ctg gtg aaa aca gca gag ctg ccc ccg gat        209
Leu Leu Asn Thr Pro Lys Leu Val Lys Thr Ala Glu Leu Pro Pro Asp
     25                  30                  35 cgg aac tac gtg ctg ggc gcc cac cct cat ggg atc atg tgt aca ggc        257
Arg Asn Tyr Val Leu Gly Ala His Pro His Gly Ile Met Cys Thr Gly
 40                  45                  50                  55 ttc ctc tgt aat ttc tcc acc gag agc aat ggc ttc tcc cag ctc ttc        305
Phe Leu Cys Asn Phe Ser Thr Glu Ser Asn Gly Phe Ser Gln Leu Phe
                 60                  65                  70 ccg ggg ctc cgg ccc tgg tta gcc gtg ctg gct ggc ctc ttc tac ctc        353
Pro Gly Leu Arg Pro Trp Leu Ala Val Leu Ala Gly Leu Phe Tyr Leu
             75                  80                  85 ccg gtc tat cgc gac tac atc atg tcc ttt ggg gcg tcc ctg gtg ccc        401
Pro Val Tyr Arg Asp Tyr Ile Met Ser Phe Gly Ala Ser Leu Val Pro
         90                  95                 100 gtg tac tcc ttt ggg gag aat gac atc ttt aga ctt aag gct ttt gcc        449
Val Tyr Ser Phe Gly Glu Asn Asp Ile Phe Arg Leu Lys Ala Phe Ala
     105                 110                 115 aca ggc tcc tgg cag cat tgg tgc cag ctc acc ttc aag aag ctc atg        497
Thr Gly Ser Trp Gln His Trp Cys Gln Leu Thr Phe Lys Lys Leu Met
120                 125                 130                 135 ggc ttc tct cct tgc atc ttc tgg ggt cgc ggt ctc ttc tca gcc acc        545
Gly Phe Ser Pro Cys Ile Phe Trp Gly Arg Gly Leu Phe Ser Ala Thr
                 140                 145                 150 tcc tgg ggc ctg ctg ccc ttt gct gtg ccc atc acc act gtg gtg ggc        593
Ser Trp Gly Leu Leu Pro Phe Ala Val Pro Ile Thr Thr Val Val Gly
             155                 160                 165 cgc ccc atc ccc gtc ccc cag cgc ctc cac ccc acc gag gag gaa gtc        641
Arg Pro Ile Pro Val Pro Gln Arg Leu His Pro Thr Glu Glu Glu Val
         170                 175                 180 aat cac tat cac gcc ctc tac atg acg gac ctg gag cag ctc ttc gag        689
Asn His Tyr His Ala Leu Tyr Met Thr Asp Leu Glu Gln Leu Phe Glu
     185                 190                 195 gag cac aag gaa agc tgt ggg gtc ccc gct tcc acc tgc ctc acc ttc        737
Glu His Lys Glu Ser Cys Gly Val Pro Ala Ser Thr Cys Leu Thr Phe
200                 205                 210                 215 atc taggcctggc cgcggccttt cgctgagccc ctgagcccaa ggcactgaga             790
Ile cctccaccca ctgtggactc catgcctcca at                                    822

<210> SEQ ID NO 4
<211> LENGTH: 216
<212> TYPE: PRT
<213> ORGANISM: human

<400> SEQUENCE: 4

Leu Gly Thr Leu Leu Gly Trp Arg Ala Pro Leu Phe Ser Arg Cys Leu
 1               5                  10                  15

Ala Phe His Pro Pro Phe Ile Leu Leu Asn Thr Pro Lys Leu Val Lys
```

```
                    20                  25                  30
Thr Ala Glu Leu Pro Pro Asp Arg Asn Tyr Val Leu Gly Ala His Pro
         35                  40                  45

His Gly Ile Met Cys Thr Gly Phe Leu Cys Asn Phe Ser Thr Glu Ser
     50                  55                  60

Asn Gly Phe Ser Gln Leu Phe Pro Gly Leu Arg Pro Trp Leu Ala Val
 65                  70                  75                  80

Leu Ala Gly Leu Phe Tyr Leu Pro Val Tyr Arg Asp Tyr Ile Met Ser
                 85                  90                  95

Phe Gly Ala Ser Leu Val Pro Val Tyr Ser Phe Gly Glu Asn Asp Ile
            100                 105                 110

Phe Arg Leu Lys Ala Phe Ala Thr Gly Ser Trp Gln His Trp Cys Gln
        115                 120                 125

Leu Thr Phe Lys Lys Leu Met Gly Phe Ser Pro Cys Ile Phe Trp Gly
    130                 135                 140

Arg Gly Leu Phe Ser Ala Thr Ser Trp Gly Leu Leu Pro Phe Ala Val
145                 150                 155                 160

Pro Ile Thr Thr Val Val Gly Arg Pro Ile Pro Val Pro Gln Arg Leu
                165                 170                 175

His Pro Thr Glu Glu Glu Val Asn His Tyr His Ala Leu Tyr Met Thr
            180                 185                 190

Asp Leu Glu Gln Leu Phe Glu Glu His Lys Glu Ser Cys Gly Val Pro
        195                 200                 205

Ala Ser Thr Cys Leu Thr Phe Ile
    210                 215

<210> SEQ ID NO 5
<211> LENGTH: 392
<212> TYPE: DNA
<213> ORGANISM: human
<220> FEATURE:
<221> NAME/KEY: CDS
<222> LOCATION: (3)..(392)
<223> OTHER INFORMATION:

<400> SEQUENCE: 5 ac tgt tct gag atc ttt gcc tcc ctc agg ctc ccg aga atc atg gct     47
   Cys Ser Glu Ile Phe Ala Ser Leu Arg Leu Pro Arg Ile Met Ala
     1               5                  10                  15 cat tcc aag cag cct agt cac ttc cag agt ctg atg ctt ctg cag tgg   95
His Ser Lys Gln Pro Ser His Phe Gln Ser Leu Met Leu Leu Gln Trp
                 20                  25                  30 cct ttg agc tac ctt gcc atc ttt tgg atc ttg cag cca ttg ttc gtc  143
Pro Leu Ser Tyr Leu Ala Ile Phe Trp Ile Leu Gln Pro Leu Phe Val
             35                  40                  45 tac ctg ctg ttt aca tcc ttg tgg ccg cta cca gtg ctt tac ttt gcc  191
Tyr Leu Leu Phe Thr Ser Leu Trp Pro Leu Pro Val Leu Tyr Phe Ala
         50                  55                  60 tgg ttg ttc ctg gac tgg aag acc cca gag cga ggt ggc agg cgt tcg  239
Trp Leu Phe Leu Asp Trp Lys Thr Pro Glu Arg Gly Gly Arg Arg Ser
 65                  70                  75 gcc tgg gta agg aac tgg tgt gtc tgg acc cac atc agg gac tat ttc  287
Ala Trp Val Arg Asn Trp Cys Val Trp Thr His Ile Arg Asp Tyr Phe
 80                  85                  90                  95 ccc att acg atc ctg aag aca aag gac cta tca cct gag cac aac tac  335
Pro Ile Thr Ile Leu Lys Thr Lys Asp Leu Ser Pro Glu His Asn Tyr
                100                 105                 110 ctc atg ggg gtt cac ccc atg ggc ctc ctg acc ttt ggc gcc ttc tgc  383
```

-continued

```
Leu Met Gly Val His Pro Met Gly Leu Leu Thr Phe Gly Ala Phe Cys
            115                 120                 125 aac ttc tgc                                                              392
Asn Phe Cys
        130

<210> SEQ ID NO 6
<211> LENGTH: 130
<212> TYPE: PRT
<213> ORGANISM: human

<400> SEQUENCE: 6

Cys Ser Glu Ile Phe Ala Ser Leu Arg Leu Pro Arg Ile Met Ala His
1               5                   10                  15

Ser Lys Gln Pro Ser His Phe Gln Ser Leu Met Leu Gln Trp Pro
            20                  25                  30

Leu Ser Tyr Leu Ala Ile Phe Trp Ile Leu Gln Pro Leu Phe Val Tyr
            35                  40                  45

Leu Leu Phe Thr Ser Leu Trp Pro Leu Pro Val Leu Tyr Phe Ala Trp
    50                  55                  60

Leu Phe Leu Asp Trp Lys Thr Pro Glu Arg Gly Arg Arg Ser Ala
65                  70                  75                  80

Trp Val Arg Asn Trp Cys Val Trp Thr His Ile Arg Asp Tyr Phe Pro
                85                  90                  95

Ile Thr Ile Leu Lys Thr Lys Asp Leu Ser Pro Glu His Asn Tyr Leu
            100                 105                 110

Met Gly Val His Pro Met Gly Leu Leu Thr Phe Gly Ala Phe Cys Asn
            115                 120                 125

Phe Cys
    130

<210> SEQ ID NO 7
<211> LENGTH: 2519
<212> TYPE: DNA
<213> ORGANISM: human
<220> FEATURE:
<221> NAME/KEY: CDS
<222> LOCATION: (714)..(1373)
<223> OTHER INFORMATION:

<400> SEQUENCE: 7
gccgcctctg ctgggtctta ggctgttct ctcgcgccac cactggccgc cggccgcagc       60
tccaggtgtc ctagccgccc agcctcgacg ccgtcccggg accctgtgc tctgcgcgaa      120 gccctggccc cggggccgg ggcatgggcc aggggcgcgg ggtgaagcgg cttcccgcgg      180
ggccgtgact gggcgggctt cagccatgaa gaccctcata gccgcctact ccggggtcct      240
gcgcggcgag cgtcaggccg aggctgaccg gagccagcgc tctcacggag gacctgcgct      300
gtcgcgcgag gggtctggga gatggggcac tggatccagc atcctctccg ccctccagga      360
cctcttctct gtcacctggc tcaataggtc caaggtggaa agcagctac aggtcatctc      420 agtgctccag tgggtcctgt ccttccttgt actgggagtg gcctgcagtg ccatcctcat      480
gtacatattc tgcactgatt gctggctcat cgctgtgctc tacttcactt ggctggtgtt      540
tgactggaac acaccaaga aaggtggcag gaggtcacag tgggtccgaa actgggctgt      600
gtggcgctac tttcgagact actttcccat ccagctggtg aagacacaca acctgctgac      660
caccaggaac tatatctttg gataccaccc ccatggtatc atgggcctgg gct gcc        716
                                                        Ala
                                                        1
```

| | |
|---|---|
| ttc tgc aac ttc agc aca gag gcc aca gaa gtg agc aag aag ttc cca<br>Phe Cys Asn Phe Ser Thr Glu Ala Thr Glu Val Ser Lys Lys Phe Pro<br>5                          10                      15 | 764 |
| ggc ata cgg cct tac ctg gct aca ctg gca ggc aac ttc cga atg cct<br>Gly Ile Arg Pro Tyr Leu Ala Thr Leu Ala Gly Asn Phe Arg Met Pro<br>        20                   25                  30 | 812 |
| gtg ttg agg gag tac ctg atg tct gga ggt atc tgc cct gtc agc cgg<br>Val Leu Arg Glu Tyr Leu Met Ser Gly Gly Ile Cys Pro Val Ser Arg<br>35                          40                      45 | 860 |
| gac acc ata gac tat ttg ctt tca aag aat ggg agt ggc aat gct atc<br>Asp Thr Ile Asp Tyr Leu Leu Ser Lys Asn Gly Ser Gly Asn Ala Ile<br>50                     55                  60                  65 | 908 |
| atc atc gtg gtc ggg ggt gcg gct gag tct ctg agc tcc atg cct ggc<br>Ile Ile Val Val Gly Gly Ala Ala Glu Ser Leu Ser Ser Met Pro Gly<br>              70                      75                      80 | 956 |
| aag aat gca gtc acc ctg cgg aac cgc aag ggc ttt gtg aaa ctg gcc<br>Lys Asn Ala Val Thr Leu Arg Asn Arg Lys Gly Phe Val Lys Leu Ala<br>        85                   90                  95 | 1004 |
| ctg cgt cat gga gct gac ctg gtt ccc atc tac tcc ttt gga gag aat<br>Leu Arg His Gly Ala Asp Leu Val Pro Ile Tyr Ser Phe Gly Glu Asn<br>100                       105                 110 | 1052 |
| gaa gtg tac aag cag gtg atc ttc gag gag ggc tcc tgg ggc cga tgg<br>Glu Val Tyr Lys Gln Val Ile Phe Glu Glu Gly Ser Trp Gly Arg Trp<br>115                     120                 125 | 1100 |
| gtc cag aag aag ttc cag aaa tac att ggt ttc gcc cca tgc atc ttc<br>Val Gln Lys Lys Phe Gln Lys Tyr Ile Gly Phe Ala Pro Cys Ile Phe<br>130                     135                 140                 145 | 1148 |
| cat ggt cga ggc ctc ttc tcc tcc gac acc tgg ggg ctg gtg ccc tac<br>His Gly Arg Gly Leu Phe Ser Ser Asp Thr Trp Gly Leu Val Pro Tyr<br>                    150                 155                 160 | 1196 |
| tcc aag ccc atc acc act gtt gtg gga gag ccc atc acc atc ccc aag<br>Ser Lys Pro Ile Thr Thr Val Val Gly Glu Pro Ile Thr Ile Pro Lys<br>165                     170                 175 | 1244 |
| ctg gag cac cca acc cag caa gac atc gac ctg tac cac acc atg tac<br>Leu Glu His Pro Thr Gln Gln Asp Ile Asp Leu Tyr His Thr Met Tyr<br>        180                   185                 190 | 1292 |
| atg gag gcc ctg gtg aag ctc ttc gac aag cac aag acc aag ttc ggc<br>Met Glu Ala Leu Val Lys Leu Phe Asp Lys His Lys Thr Lys Phe Gly<br>195                     200                 205 | 1340 |
| ctc ccg gag act gag gtc ctg gag gtg aac tga gccagccttc ggggccaatt<br>Leu Pro Glu Thr Glu Val Leu Glu Val Asn<br>210                     215 | 1393 |
| ccctggagga accagctgca aatcactttt ttgctctgta aatttggaag tgtcatgggt | 1453 |
| gtctgtgggt tatttaaaag aaattataac aattttgcta aaccattaca atgttaggtc | 1513 |
| ttttttaaga aggaaaaagt cagtatttca agttctttca cttccagctt gccctgttct | 1573 |
| aggtggtggc taaatctggg cctaatctgg gtggctcagc taacctctct tcttcccttc | 1633 |
| ctgaagtgac aaaggaaact cagtcttctt ggggaagaag gattgccatt agtgacttgg | 1693 |
| accagttaga tgattcactt tttgccccta gggatgagag gcgaaagcca cttctcatac | 1753 |
| aagccccttt attgccacta ccccacgctc gtctagtcct gaaactgcag gaccagtttc | 1813 |
| tctgccaagg ggaggagttg gagagcacag ttgccccgtt gtgtgagggc agtagtaggc | 1873 |
| atctggaatg ctccagtttg atctcccttc tgccaccoct acctcacccc tagtcactca | 1933 |
| tatcggagcc tggactggcc tccaggatga ggatgggggt ggcaatgaca ccctgcaggg | 1993 |
| gaaaggactg ccccccatgc accattgcag ggaggatgcc gccaccatga gctaggtgga | 2053 |

```
gtaactggtt tttcttgggt ggctgatgac atggatgcag cacagactca gccttggcct    2113
ggagcacatg cttactggtg gcctcagttt accttcccca gatcctagat tctggatgtg    2173
aggaagagat ccctcttcag aaggggcctg gccttctgag cagcagatta gttccaaagc    2233
aggtggcccc cgaacccaag cctcactttt ctgtgccttc ctgaggggt tgggccgggg     2293 aggaaaccca accctctcct gtgtgttctg ttatctcttg atgagatcat tgcaccatgt    2353 cagactttg tatatgcctt gaaataaat gaaagtgaga catggtgcaa tgatctcatc      2413
aagagataac agaacagaca ggagagggtt gggttatctc ttgatgagat cattgcacca   2473
tgtcagactt ttgtatatgc cttgaaaata aatgaaagtg agaatc                  2519
```

```
<210> SEQ ID NO 8
<211> LENGTH: 219
<212> TYPE: PRT
<213> ORGANISM: human

<400> SEQUENCE: 8

Ala Phe Cys Asn Phe Ser Thr Glu Ala Thr Glu Val Ser Lys Lys Phe
  1               5                  10                  15

Pro Gly Ile Arg Pro Tyr Leu Ala Thr Leu Ala Gly Asn Phe Arg Met
             20                  25                  30

Pro Val Leu Arg Glu Tyr Leu Met Ser Gly Gly Ile Cys Pro Val Ser
         35                  40                  45

Arg Asp Thr Ile Asp Tyr Leu Leu Ser Lys Asn Gly Ser Gly Asn Ala
     50                  55                  60

Ile Ile Ile Val Val Gly Ala Ala Glu Ser Leu Ser Ser Met Pro
 65                  70                  75                  80

Gly Lys Asn Ala Val Thr Leu Arg Asn Arg Lys Gly Phe Val Lys Leu
                 85                  90                  95

Ala Leu Arg His Gly Ala Asp Leu Val Pro Ile Tyr Ser Phe Gly Glu
            100                 105                 110

Asn Glu Val Tyr Lys Gln Val Ile Phe Glu Glu Gly Ser Trp Gly Arg
        115                 120                 125

Trp Val Gln Lys Lys Phe Gln Lys Tyr Ile Gly Phe Ala Pro Cys Ile
    130                 135                 140

Phe His Gly Arg Gly Leu Phe Ser Ser Asp Thr Trp Gly Leu Val Pro
145                 150                 155                 160

Tyr Ser Lys Pro Ile Thr Thr Val Val Gly Glu Pro Ile Thr Ile Pro
                165                 170                 175

Lys Leu Glu His Pro Thr Gln Gln Asp Ile Asp Leu Tyr His Thr Met
            180                 185                 190

Tyr Met Glu Ala Leu Val Lys Leu Phe Asp Lys His Lys Thr Lys Phe
        195                 200                 205

Gly Leu Pro Glu Thr Glu Val Leu Glu Val Asn
    210                 215

<210> SEQ ID NO 9
<211> LENGTH: 685
<212> TYPE: DNA
<213> ORGANISM: human
<220> FEATURE:
<221> NAME/KEY: misc_feature
<222> LOCATION: (292)..(292)
<223> OTHER INFORMATION: n = a, c, g ot t
<220> FEATURE:
<221> NAME/KEY: misc_feature
<222> LOCATION: (293)..(293)
<223> OTHER INFORMATION: n = a, c, g ot t
```

```
<220> FEATURE:
<221> NAME/KEY: misc_feature
<222> LOCATION: (341)..(341)
<223> OTHER INFORMATION: n = a, c, g ot t
<220> FEATURE:
<221> NAME/KEY: CDS
<222> LOCATION: (2)..(322)
<223> OTHER INFORMATION: n = a, c, g ot t

<400> SEQUENCE: 9
```

```
g cgg aac cgc aag ggc ttt gtg aaa ctg gcc ctg cgt cat gga gct gac        49
  Arg Asn Arg Lys Gly Phe Val Lys Leu Ala Leu Arg His Gly Ala Asp
  1               5                  10                  15 ctg gtt ccc atc tac tcc ttt gga gag aat gaa gtg tac aag cag gtg          97
Leu Val Pro Ile Tyr Ser Phe Gly Glu Asn Glu Val Tyr Lys Gln Val
             20                  25                  30 atc ttc gag gag ggc tcc tgg ggc cga tgg gtc cag aag aag ttc cag         145
Ile Phe Glu Glu Gly Ser Trp Gly Arg Trp Val Gln Lys Lys Phe Gln
         35                  40                  45 aaa tac att ggt ttc gcc cca tgc atc ttc cat ggt cga ggc ctc ttc         193
Lys Tyr Ile Gly Phe Ala Pro Cys Ile Phe His Gly Arg Gly Leu Phe
     50                  55                  60 tcc tcc gac acc tgg ggg ctg gtg ccc tac tcc aag ccc atc acc act         241
Ser Ser Asp Thr Trp Gly Leu Val Pro Tyr Ser Lys Pro Ile Thr Thr
65                  70                  75                  80 gtt ggt ggt gga aaa att cag tct agg agt aaa aaa agg aag atc aac         289
Val Gly Gly Gly Lys Ile Gln Ser Arg Ser Lys Lys Arg Lys Ile Asn
                 85                  90                  95 atn ntg cag aat gac tca tgc tat tca tta tag aagcaattgc tggagatgnt      342
Xaa Xaa Gln Asn Asp Ser Cys Tyr Ser Leu
             100                 105 atcattgtgg atcacggaag tcttcatgga agaggtggca tttgagctgg gccttcactg       402
aagcggtgaa tcggcgtcct gggtgcctgg cacaccttgt agctcagctt actagctagt       462
ggagtgcgaa ggggcgtgta cttgtcggtt ggagctggtc atgaaagagc tcgtgggact       522
gcccgacggt tctcaggtcc cagtgcatcc tgcgtggtgg ctctctgctg aaccataaag       582
cattcctttt caatccctgc acgctcacgc cgggaaaaga ctgcacaagg ggctccaagg       642
cagacaagcg atcgccaccc agctggcttc cgagggtccc cgc                         685

<210> SEQ ID NO 10
<211> LENGTH: 106
<212> TYPE: PRT
<213> ORGANISM: human
<220> FEATURE:
<221> NAME/KEY: misc_feature
<222> LOCATION: (97)..(97)
<223> OTHER INFORMATION: The 'Xaa' at location 97 stands for Ile, or
      Met.
<220> FEATURE:
<221> NAME/KEY: misc_feature
<222> LOCATION: (98)..(98)
<223> OTHER INFORMATION: The 'Xaa' at location 98 stands for Met, Val,
      or Leu.
<220> FEATURE:
<221> NAME/KEY: misc_feature
<222> LOCATION: (292)..(292)
<223> OTHER INFORMATION: n = a, c, g ot t
<220> FEATURE:
<221> NAME/KEY: misc_feature
<222> LOCATION: (293)..(293)
<223> OTHER INFORMATION: n = a, c, g ot t
<220> FEATURE:
<221> NAME/KEY: misc_feature
<222> LOCATION: (341)..(341)
<223> OTHER INFORMATION: n = a, c, g ot t
```

```
<400> SEQUENCE: 10

Arg Asn Arg Lys Gly Phe Val Lys Leu Ala Leu Arg His Gly Ala Asp
1               5                   10                  15

Leu Val Pro Ile Tyr Ser Phe Gly Glu Asn Glu Val Tyr Lys Gln Val
            20                  25                  30

Ile Phe Glu Glu Gly Ser Trp Gly Arg Trp Val Gln Lys Lys Phe Gln
        35                  40                  45

Lys Tyr Ile Gly Phe Ala Pro Cys Ile Phe His Gly Arg Gly Leu Phe
    50                  55                  60

Ser Ser Asp Thr Trp Gly Leu Val Pro Tyr Ser Lys Pro Ile Thr Thr
65                  70                  75                  80

Val Gly Gly Lys Ile Gln Ser Arg Ser Lys Arg Lys Ile Asn
            85                  90                  95

Xaa Xaa Gln Asn Asp Ser Cys Tyr Ser Leu
            100                 105

<210> SEQ ID NO 11
<211> LENGTH: 474
<212> TYPE: DNA
<213> ORGANISM: human
<220> FEATURE:
<221> NAME/KEY: CDS
<222> LOCATION: (2)..(442)
<223> OTHER INFORMATION:

<400> SEQUENCE: 11 a aaa gaa tca ctg gat gct cat cct gga aag ttc act ctg ttc atc cgc       49
  Lys Glu Ser Leu Asp Ala His Pro Gly Lys Phe Thr Leu Phe Ile Arg
  1               5                   10                  15 cag cgg aaa gga ttt gtt aaa att gct ttg acc cat ggc gcc tct ctg        97
Gln Arg Lys Gly Phe Val Lys Ile Ala Leu Thr His Gly Ala Ser Leu
            20                  25                  30 gtc cca gtg gtt tct ttt ggt gaa aat gaa ctg ttt aaa caa act gac       145
Val Pro Val Val Ser Phe Gly Glu Asn Glu Leu Phe Lys Gln Thr Asp
        35                  40                  45 aac cct gaa gga tca tgg att aga act gtt cag aat aaa ctg cag aag       193
Asn Pro Glu Gly Ser Trp Ile Arg Thr Val Gln Asn Lys Leu Gln Lys
    50                  55                  60 atc atg ggg ttt gct ttg ccc ctg ttt cat gcc agg gga gtt ttt cag       241
Ile Met Gly Phe Ala Leu Pro Leu Phe His Ala Arg Gly Val Phe Gln
65                  70                  75                  80 tac aat ttt ggc cta atg acc tat agg aaa gcc atc cac act gtt gtt       289
Tyr Asn Phe Gly Leu Met Thr Tyr Arg Lys Ala Ile His Thr Val Val
            85                  90                  95 ggc cgc ccg atc cct gtt cgt cag act ctg aac ccg acc cag gag cag       337
Gly Arg Pro Ile Pro Val Arg Gln Thr Leu Asn Pro Thr Gln Glu Gln
            100                 105                 110 att gag gag tta cat cag acc tat atg gag gaa ctt agg aaa ttg ttt       385
Ile Glu Glu Leu His Gln Thr Tyr Met Glu Glu Leu Arg Lys Leu Phe
            115                 120                 125 gag gaa cac aaa gga aag tat ggc att cca gag cac gag act ctt gtt       433
Glu Glu His Lys Gly Lys Tyr Gly Ile Pro Glu His Glu Thr Leu Val
            130                 135                 140 tta aaa tga cttgactata aaaaaaaaaa aaaagcggcc gc                       474
Leu Lys
145

<210> SEQ ID NO 12
<211> LENGTH: 146
<212> TYPE: PRT
```

<213> ORGANISM: human

<400> SEQUENCE: 12

| Lys | Glu | Ser | Leu | Asp | Ala | His | Pro | Gly | Lys | Phe | Thr | Leu | Phe | Ile | Arg |
| 1 | | | | 5 | | | | | 10 | | | | | 15 | |

| Gln | Arg | Lys | Gly | Phe | Val | Lys | Ile | Ala | Leu | Thr | His | Gly | Ala | Ser | Leu |
| | | | 20 | | | | | 25 | | | | | 30 | | |

| Val | Pro | Val | Val | Ser | Phe | Gly | Glu | Asn | Glu | Leu | Phe | Lys | Gln | Thr | Asp |
| | | | 35 | | | | | 40 | | | | | 45 | | |

| Asn | Pro | Glu | Gly | Ser | Trp | Ile | Arg | Thr | Val | Gln | Asn | Lys | Leu | Gln | Lys |
| | 50 | | | | | 55 | | | | | 60 | | | | |

| Ile | Met | Gly | Phe | Ala | Leu | Pro | Leu | Phe | His | Ala | Arg | Gly | Val | Phe | Gln |
| 65 | | | | | 70 | | | | | 75 | | | | | 80 |

| Tyr | Asn | Phe | Gly | Leu | Met | Thr | Tyr | Arg | Lys | Ala | Ile | His | Thr | Val | Val |
| | | | | 85 | | | | | 90 | | | | | 95 | |

| Gly | Arg | Pro | Ile | Pro | Val | Arg | Gln | Thr | Leu | Asn | Pro | Thr | Gln | Glu | Gln |
| | | | 100 | | | | | 105 | | | | | 110 | | |

| Ile | Glu | Glu | Leu | His | Gln | Thr | Tyr | Met | Glu | Glu | Leu | Arg | Lys | Leu | Phe |
| | | | 115 | | | | | 120 | | | | | 125 | | |

| Glu | Glu | His | Lys | Gly | Lys | Tyr | Gly | Ile | Pro | Glu | His | Glu | Thr | Leu | Val |
| | 130 | | | | | 135 | | | | | 140 | | | | |

| Leu | Lys |
| 145 | |

<210> SEQ ID NO 13
<211> LENGTH: 254
<212> TYPE: DNA
<213> ORGANISM: human
<220> FEATURE:
<221> NAME/KEY: misc_feature
<222> LOCATION: (153)..(153)
<223> OTHER INFORMATION: n = a,c,g or t
<220> FEATURE:
<221> NAME/KEY: misc_feature
<222> LOCATION: (153)..(153)
<223> OTHER INFORMATION: n = a, c, g or t
<220> FEATURE:
<221> NAME/KEY: CDS
<222> LOCATION: (3)..(254)
<223> OTHER INFORMATION:

<400> SEQUENCE: 13

```
gc aac ctc ttc gag gcc cac aaa ctt aag ttc aac atc att gta ggg        47
   Asn Leu Phe Glu Ala His Lys Leu Lys Phe Asn Ile Ile Val Gly
   1               5                   10                  15 ggt gcc cag gag gcc ctg gat gcc agg cct gga tcc ttc acg ctg tta       95
Gly Ala Gln Glu Ala Leu Asp Ala Arg Pro Gly Ser Phe Thr Leu Leu
            20                  25                  30 ctg cgg aac cga aag ggc ttc gtc agg ctc gcc ctg aca cac ggg gca       143
Leu Arg Asn Arg Lys Gly Phe Val Arg Leu Ala Leu Thr His Gly Ala
        35                  40                  45 ccc ctg gtt nta atc ttc tcc ttc ggg gag aat gac cta ttt gac cag       191
Pro Leu Val Xaa Ile Phe Ser Phe Gly Glu Asn Asp Leu Phe Asp Gln
    50                  55                  60 att ccc aac tct tct ggc tcc tgg tta cgc tat atc cag aat cgg ttg       239
Ile Pro Asn Ser Ser Gly Ser Trp Leu Arg Tyr Ile Gln Asn Arg Leu
65                  70                  75 cag aag atc atg ggc                                                   254
Gln Lys Ile Met Gly
80
```

```
<210> SEQ ID NO 14
<211> LENGTH: 84
<212> TYPE: PRT
<213> ORGANISM: human
<220> FEATURE:
<221> NAME/KEY: misc_feature
<222> LOCATION: (51)..(51)
<223> OTHER INFORMATION: The 'Xaa' at location 51 stands for Ile, Val,
      or Leu.
<220> FEATURE:
<221> NAME/KEY: misc_feature
<222> LOCATION: (153)..(153)
<223> OTHER INFORMATION: n = a,c,g or t
<220> FEATURE:
<221> NAME/KEY: misc_feature
<222> LOCATION: (153)..(153)
<223> OTHER INFORMATION: n = a, c, g or t

<400> SEQUENCE: 14

Asn Leu Phe Glu Ala His Lys Leu Lys Phe Asn Ile Ile Val Gly Gly
 1               5                  10                  15

Ala Gln Glu Ala Leu Asp Ala Arg Pro Gly Ser Phe Thr Leu Leu Leu
            20                  25                  30

Arg Asn Arg Lys Gly Phe Val Arg Leu Ala Leu Thr His Gly Ala Pro
        35                  40                  45

Leu Val Xaa Ile Phe Ser Phe Gly Glu Asn Asp Leu Phe Asp Gln Ile
    50                  55                  60

Pro Asn Ser Ser Gly Ser Trp Leu Arg Tyr Ile Gln Asn Arg Leu Gln
65                  70                  75                  80

Lys Ile Met Gly

<210> SEQ ID NO 15
<211> LENGTH: 887
<212> TYPE: DNA
<213> ORGANISM: human
<220> FEATURE:
<221> NAME/KEY: CDS
<222> LOCATION: (314)..(805)
<223> OTHER INFORMATION:

<400> SEQUENCE: 15
ggctgtttca gcatggcggt gcctccatgt ggccttttgg tgtcttcatg ttatatcctg    60
tccaggtggt gttggtataa ataattctag gcaccatcat acctgagttt ctcagtagcc   120
ctaggaggta gcaggacag gtccaaatac tctattgcca ctttacaaat gaagagcctg   180
taggagaggg aagcaatttg tcccaagcca gcatcaagtc tgtggcacag ccagcaccat   240
aatatctcca ggtgctgtca cataccatat ctgaatcttc gtaagaaccc agggtggtca   300
gacatatgga tga aga cct gga ggc tca gag ggg agg ttt ccc aag gtc      349
            Arg Pro Gly Gly Ser Glu Gly Arg Phe Pro Lys Val
              1               5                  10 aca cca gtg agt ggc aga gtc agg gct ggt aca cag gcc ccg ccc tgg    397
Thr Pro Val Ser Gly Arg Val Arg Ala Gly Thr Gln Ala Pro Pro Trp
            15                  20                  25 ctc agc agg ttg ccg tcc ctg cag ctg gtc aag act gct gag ctg gac    445
Leu Ser Arg Leu Pro Ser Leu Gln Leu Val Lys Thr Ala Glu Leu Asp
    30                  35                  40 ccc tct cgg aac tac att gcg ggc ttc cac ccc cat gga gtc ctg gca    493
Pro Ser Arg Asn Tyr Ile Ala Gly Phe His Pro His Gly Val Leu Ala
45                  50                  55                  60 gtc gga gcc ttt gcc aac ctg tgc act gag agc aca ggc ttc tct tcg    541
Val Gly Ala Phe Ala Asn Leu Cys Thr Glu Ser Thr Gly Phe Ser Ser
            65                  70                  75
```

```
atc ttc ccc ggt atc cgc ccc cat ctg atg atg ctg acc ttg tgg ttc      589
Ile Phe Pro Gly Ile Arg Pro His Leu Met Met Leu Thr Leu Trp Phe
            80                  85                  90 cgg gcc ccc ttc ttc aga gat tac atc atg tct gca ggg ttg gtc aca      637
Arg Ala Pro Phe Phe Arg Asp Tyr Ile Met Ser Ala Gly Leu Val Thr
        95                 100                 105 tca gaa aag gag agt gct gct cac att ctg aac agg aag ggt ggc gga      685
Ser Glu Lys Glu Ser Ala Ala His Ile Leu Asn Arg Lys Gly Gly Gly
    110                 115                 120 aac ttg ctg ggc atc att gta ggg ggt gcc cag gag gcc ctg gat gcc      733
Asn Leu Leu Gly Ile Ile Val Gly Gly Ala Gln Glu Ala Leu Asp Ala
125                 130                 135                 140 agg cct gga tcc ttc acg ctg tta ctg cgg aac cga aag ggc ttc gtc      781
Arg Pro Gly Ser Phe Thr Leu Leu Leu Arg Asn Arg Lys Gly Phe Val
                145                 150                 155 agg ctc gcc ctg aca cac ggg tat caagcctctg ggaagagcac tctgggttca    835
Arg Leu Ala Leu Thr His Gly Tyr
                160 gttggcaatt ggcaagcgat ctttattttg gtgggaagat ggcagagacg aa           887
```

<210> SEQ ID NO 16
<211> LENGTH: 164
<212> TYPE: PRT
<213> ORGANISM: human

<400> SEQUENCE: 16

```
Arg Pro Gly Gly Ser Glu Gly Arg Phe Pro Lys Val Thr Pro Val Ser
1               5                   10                  15

Gly Arg Val Arg Ala Gly Thr Gln Ala Pro Pro Trp Leu Ser Arg Leu
            20                  25                  30

Pro Ser Leu Gln Leu Val Lys Thr Ala Glu Leu Asp Pro Ser Arg Asn
        35                  40                  45

Tyr Ile Ala Gly Phe His Pro His Gly Val Leu Ala Val Gly Ala Phe
    50                  55                  60

Ala Asn Leu Cys Thr Glu Ser Thr Gly Phe Ser Ser Ile Phe Pro Gly
65                  70                  75                  80

Ile Arg Pro His Leu Met Met Leu Thr Leu Trp Phe Arg Ala Pro Phe
                85                  90                  95

Phe Arg Asp Tyr Ile Met Ser Ala Gly Leu Val Thr Ser Glu Lys Glu
            100                 105                 110

Ser Ala Ala His Ile Leu Asn Arg Lys Gly Gly Gly Asn Leu Leu Gly
        115                 120                 125

Ile Ile Val Gly Gly Ala Gln Glu Ala Leu Asp Ala Arg Pro Gly Ser
    130                 135                 140

Phe Thr Leu Leu Leu Arg Asn Arg Lys Gly Phe Val Arg Leu Ala Leu
145                 150                 155                 160

Thr His Gly Tyr
```

<210> SEQ ID NO 17
<211> LENGTH: 446
<212> TYPE: DNA
<213> ORGANISM: human
<220> FEATURE:
<221> NAME/KEY: CDS
<222> LOCATION: (1)..(444)
<223> OTHER INFORMATION:

<400> SEQUENCE: 17

```
agc gat tat gtc cct ctc aag ctt ctg aag act cat gac atc tgc ccc      48
```

-continued

```
Ser Asp Tyr Val Pro Leu Lys Leu Leu Lys Thr His Asp Ile Cys Pro
1               5                   10                  15 agc cgc aac tac atc ctc gtc tgc cac cct cat ggg ctc ttt gcc cat        96
Ser Arg Asn Tyr Ile Leu Val Cys His Pro His Gly Leu Phe Ala His
            20                  25                  30 gga tgg ttt ggc cac ttt gcc aca gag gcc tca ggc ttc tcc aag ata       144
Gly Trp Phe Gly His Phe Ala Thr Glu Ala Ser Gly Phe Ser Lys Ile
        35                  40                  45 ttt cct ggc atc acc cct tac ata ctc aca ctg gga gcc ttt ttc tgg       192
Phe Pro Gly Ile Thr Pro Tyr Ile Leu Thr Leu Gly Ala Phe Phe Trp
    50                  55                  60 atg cct ttc ctc aga gaa tat gta atg tct aca ggg gcc tgc tct gtg       240
Met Pro Phe Leu Arg Glu Tyr Val Met Ser Thr Gly Ala Cys Ser Val
65                  70                  75                  80 agt cga tcc tcc att gac ttt ctg ctg act cat aaa ggc aca ggc aac       288
Ser Arg Ser Ser Ile Asp Phe Leu Leu Thr His Lys Gly Thr Gly Asn
                85                  90                  95 atg gtc att gtg gtg att ggt gga ctg gct gag tgc aga tac agc ctg       336
Met Val Ile Val Val Ile Gly Gly Leu Ala Glu Cys Arg Tyr Ser Leu
            100                 105                 110 cca ggt tct tct acc ctg gtg ttg aag aac cgg tct ggc ttt gtg cgc       384
Pro Gly Ser Ser Thr Leu Val Leu Lys Asn Arg Ser Gly Phe Val Arg
        115                 120                 125 atg gcc ctt cag cat ggg gtg cct cta ata cct gcc tat gcc ttt ggg       432
Met Ala Leu Gln His Gly Val Pro Leu Ile Pro Ala Tyr Ala Phe Gly
    130                 135                 140 gag acg gac ctc ta                                                    446
Glu Thr Asp Leu
145
```

<210> SEQ ID NO 18
<211> LENGTH: 148
<212> TYPE: PRT
<213> ORGANISM: human

<400> SEQUENCE: 18

```
Ser Asp Tyr Val Pro Leu Lys Leu Leu Lys Thr His Asp Ile Cys Pro
1               5                   10                  15

Ser Arg Asn Tyr Ile Leu Val Cys His Pro His Gly Leu Phe Ala His
            20                  25                  30

Gly Trp Phe Gly His Phe Ala Thr Glu Ala Ser Gly Phe Ser Lys Ile
        35                  40                  45

Phe Pro Gly Ile Thr Pro Tyr Ile Leu Thr Leu Gly Ala Phe Phe Trp
    50                  55                  60

Met Pro Phe Leu Arg Glu Tyr Val Met Ser Thr Gly Ala Cys Ser Val
65                  70                  75                  80

Ser Arg Ser Ser Ile Asp Phe Leu Leu Thr His Lys Gly Thr Gly Asn
                85                  90                  95

Met Val Ile Val Val Ile Gly Gly Leu Ala Glu Cys Arg Tyr Ser Leu
            100                 105                 110

Pro Gly Ser Ser Thr Leu Val Leu Lys Asn Arg Ser Gly Phe Val Arg
        115                 120                 125

Met Ala Leu Gln His Gly Val Pro Leu Ile Pro Ala Tyr Ala Phe Gly
    130                 135                 140

Glu Thr Asp Leu
145
```

<210> SEQ ID NO 19

```
<211> LENGTH: 1670
<212> TYPE: DNA
<213> ORGANISM: human
<220> FEATURE:
<221> NAME/KEY: misc_feature
<222> LOCATION: (1667)..(1667)
<223> OTHER INFORMATION: n = a, c, g or t
<220> FEATURE:
<221> NAME/KEY: CDS
<222> LOCATION: (635)..(1666)
<223> OTHER INFORMATION:

<400> SEQUENCE: 19
```

| | | |
|---|---|---|
| gggaagagaa tatcgttttt cttgcaaaat acacgctaaa aactatttag aagcaaaagg | 60 |
| ttgtaatctc tgtgatgtat tctcaaatac aaacatatat gtatatactt acatttttac | 120 |
| atttaaagat aaatcaaacg taaaatgttg acaatgggta gatgtagatg aagattaaac | 180 |
| aagactttat taaataatc ttgttttttc aaaataaaaa gtttaattaa aaaacctcca | 240 |
| tcaagagttt ttgtagcaat aaacaagctg attcaaaaat ttatatagaa aaacaaagaa | 300 |
| actacaaata attaaaacaa ttttgagaac gaataaagtt aaaggaatta taccatctga | 360 |
| ttttgagact tagcataaga ctagagcaat caagacagtg atgtatttgt gaaggaatag | 420 |
| atatattgat ccacagaaca gaaaagagtc aagaaataaa cacatgaata tggtcaattg | 480 |
| atttttgaca aagatgaaaa agcaattcca tggaggatga ataagtgctt ttcaaggaac | 540 |
| ggtgtaggaa aatttgatgt ccatatgtgg caaaatgaat cttgacccaa acttcaggct | 600 |
| ctataaaaat taactcaagt atgacatcaa caag atg gtg aat ggg aag tcc atc | 655 |
| | Met Val Asn Gly Lys Ser Ile | |
| | 1            5 | |

```
aca tct ctc cag agc aac aag aat ctg gca gcc atc cat gga cca aag      703
Thr Ser Leu Gln Ser Asn Lys Asn Leu Ala Ala Ile His Gly Pro Lys
         10                  15                  20 tac ctt tgt ggg aat ttt gga ccc agg tgg cag gcg ttc agc ttg ggt      751
Tyr Leu Cys Gly Asn Phe Gly Pro Arg Trp Gln Ala Phe Ser Leu Gly
     25                  30                  35 acg aaa ctg gac cct atg gaa gta ttt ccg aaa tta ctt ccc agt aaa      799
Thr Lys Leu Asp Pro Met Glu Val Phe Pro Lys Leu Leu Pro Ser Lys
 40                  45                  50                  55 gtc cct gtt gcc cag acc ctt gct ccc tac tca gct cca tgt ttt cag      847
Val Pro Val Ala Gln Thr Leu Ala Pro Tyr Ser Ala Pro Cys Phe Gln
                 60                  65                  70 agg ctt tgg tgg tca gca gcg aag gtc aag gcc ccg agt cat aat gca      895
Arg Leu Trp Trp Ser Ala Ala Lys Val Lys Ala Pro Ser His Asn Ala
             75                  80                  85 aag caa ggg ccc aag atg gat ggg cag ctg gtg aag act cat gat ctt      943
Lys Gln Gly Pro Lys Met Asp Gly Gln Leu Val Lys Thr His Asp Leu
         90                  95                 100 tct ccc aaa cac aac tac atc att gcc aat cac ccc cat ggc att ctc      991
Ser Pro Lys His Asn Tyr Ile Ile Ala Asn His Pro His Gly Ile Leu
     105                 110                 115 tct ttt ggt gtc ttc atc aac ttt gcc act gag gcc act ggc att gct     1039
Ser Phe Gly Val Phe Ile Asn Phe Ala Thr Glu Ala Thr Gly Ile Ala
120                 125                 130                 135 cgg att ttc cca tcc atc act ccc ttt gta ggg acc tta gaa agg ata     1087
Arg Ile Phe Pro Ser Ile Thr Pro Phe Val Gly Thr Leu Glu Arg Ile
                 140                 145                 150 ttt tgg atc cca att gtg cga gaa tat gtg atg tca atg ggt gtg tgc     1135
Phe Trp Ile Pro Ile Val Arg Glu Tyr Val Met Ser Met Gly Val Cys
             155                 160                 165 cct gtg agt agc tca gcc ttg aag tac ttg ctg acc cag aaa ggc tca     1183
```

-continued

|  |  |  |  |  |  |  |  |  |  |  |  |  |  |  |  |
|---|---|---|---|---|---|---|---|---|---|---|---|---|---|---|---|
| Pro | Val | Ser | Ser | Ala | Leu | Lys | Tyr | Leu | Leu | Thr | Gln | Lys | Gly | Ser |  |
|  | 170 |  |  |  | 175 |  |  |  |  | 180 |  |  |  |  |  |

```
ggc aat gcc gtg gtt att gtg gtg ggt gga gct gct gaa gct ctc ttg    1231
Gly Asn Ala Val Val Ile Val Val Gly Gly Ala Ala Glu Ala Leu Leu
        185                 190                 195 tgc cga cca gga gcc tcc act ctc ttc ctc aag cag cgt aaa ggt ttt    1279
Cys Arg Pro Gly Ala Ser Thr Leu Phe Leu Lys Gln Arg Lys Gly Phe
200                 205                 210                 215 gtg aag atg gca ctg caa aca ggg gca tac ctt gtc cct tca tat tcc    1327
Val Lys Met Ala Leu Gln Thr Gly Ala Tyr Leu Val Pro Ser Tyr Ser
                220                 225                 230 ttt ggt gag aac gaa gtt ttc aat cag gag acc ttc cct gag ggc acg    1375
Phe Gly Glu Asn Glu Val Phe Asn Gln Glu Thr Phe Pro Glu Gly Thr
            235                 240                 245 tgg tta agg ttg ttc caa aaa acc ttc cag gac aca ttc aaa aaa atc    1423
Trp Leu Arg Leu Phe Gln Lys Thr Phe Gln Asp Thr Phe Lys Lys Ile
        250                 255                 260 ctg gga cta aat ttc tgt acc ttc cat ggc cgg ggc ttc act cgc gga    1471
Leu Gly Leu Asn Phe Cys Thr Phe His Gly Arg Gly Phe Thr Arg Gly
    265                 270                 275 tcc tgg ggc ttc ctg cct ttc aat cgg ccc att acc act gtt gtt ggg    1519
Ser Trp Gly Phe Leu Pro Phe Asn Arg Pro Ile Thr Thr Val Val Gly
280                 285                 290                 295 gaa ccc ctt cca att ccc agg att aag agg cca aac cag aag aca gta    1567
Glu Pro Leu Pro Ile Pro Arg Ile Lys Arg Pro Asn Gln Lys Thr Val
                300                 305                 310 gac aag tat cac gca ctc tac atc agt gcc ctg cgc aag ctc ttt gac    1615
Asp Lys Tyr His Ala Leu Tyr Ile Ser Ala Leu Arg Lys Leu Phe Asp
            315                 320                 325 caa cac aaa gtt gaa tat ggc ctc cct gag acc caa gag ctg aca att    1663
Gln His Lys Val Glu Tyr Gly Leu Pro Glu Thr Gln Glu Leu Thr Ile
        330                 335                 340 aca ntaa                                                           1670
Thr
```

<210> SEQ ID NO 20
<211> LENGTH: 344
<212> TYPE: PRT
<213> ORGANISM: human
<220> FEATURE:
<221> NAME/KEY: misc_feature
<222> LOCATION: (1667)..(1667)
<223> OTHER INFORMATION: n = a, c, g or t

<400> SEQUENCE: 20

|  |  |  |  |  |  |  |  |  |  |  |  |  |  |  |
|---|---|---|---|---|---|---|---|---|---|---|---|---|---|---|
| Met | Val | Asn | Gly | Lys | Ser | Ile | Thr | Ser | Leu | Gln | Ser | Asn | Lys | Asn | Leu |
| 1 |  |  |  | 5 |  |  |  |  | 10 |  |  |  |  | 15 |  |
| Ala | Ala | Ile | His | Gly | Pro | Lys | Tyr | Leu | Cys | Gly | Asn | Phe | Gly | Pro | Arg |
|  |  |  | 20 |  |  |  |  | 25 |  |  |  |  | 30 |  |  |
| Trp | Gln | Ala | Phe | Ser | Leu | Gly | Thr | Lys | Leu | Asp | Pro | Met | Glu | Val | Phe |
|  |  |  | 35 |  |  |  |  | 40 |  |  |  |  | 45 |  |  |
| Pro | Lys | Leu | Leu | Pro | Ser | Lys | Val | Pro | Val | Ala | Gln | Thr | Leu | Ala | Pro |
|  | 50 |  |  |  |  | 55 |  |  |  |  | 60 |  |  |  |  |
| Tyr | Ser | Ala | Pro | Cys | Phe | Gln | Arg | Leu | Trp | Trp | Ser | Ala | Ala | Lys | Val |
| 65 |  |  |  |  | 70 |  |  |  |  | 75 |  |  |  |  | 80 |
| Lys | Ala | Pro | Ser | His | Asn | Ala | Lys | Gln | Gly | Pro | Lys | Met | Asp | Gly | Gln |
|  |  |  |  | 85 |  |  |  |  | 90 |  |  |  |  | 95 |  |
| Leu | Val | Lys | Thr | His | Asp | Leu | Ser | Pro | Lys | His | Asn | Tyr | Ile | Ile | Ala |
|  |  |  | 100 |  |  |  |  | 105 |  |  |  |  | 110 |  |  |

-continued

```
Asn His Pro His Gly Ile Leu Ser Phe Gly Val Phe Ile Asn Phe Ala
        115                 120                 125

Thr Glu Ala Thr Gly Ile Ala Arg Ile Phe Pro Ser Ile Thr Pro Phe
    130                 135                 140

Val Gly Thr Leu Glu Arg Ile Phe Trp Ile Pro Ile Val Arg Glu Tyr
145                 150                 155                 160

Val Met Ser Met Gly Val Cys Pro Val Ser Ser Ser Ala Leu Lys Tyr
                165                 170                 175

Leu Leu Thr Gln Lys Gly Ser Gly Asn Ala Val Val Ile Val Val Gly
            180                 185                 190

Gly Ala Ala Glu Ala Leu Leu Cys Arg Pro Gly Ala Ser Thr Leu Phe
        195                 200                 205

Leu Lys Gln Arg Lys Gly Phe Val Lys Met Ala Leu Gln Thr Gly Ala
    210                 215                 220

Tyr Leu Val Pro Ser Tyr Ser Phe Gly Glu Asn Glu Val Phe Asn Gln
225                 230                 235                 240

Glu Thr Phe Pro Glu Gly Thr Trp Leu Arg Leu Phe Gln Lys Thr Phe
                245                 250                 255

Gln Asp Thr Phe Lys Lys Ile Leu Gly Leu Asn Phe Cys Thr Phe His
            260                 265                 270

Gly Arg Gly Phe Thr Arg Gly Ser Trp Gly Phe Leu Pro Phe Asn Arg
        275                 280                 285

Pro Ile Thr Thr Val Val Gly Glu Pro Leu Pro Ile Pro Arg Ile Lys
        290                 295                 300

Arg Pro Asn Gln Lys Thr Val Asp Lys Tyr His Ala Leu Tyr Ile Ser
305                 310                 315                 320

Ala Leu Arg Lys Leu Phe Asp Gln His Lys Val Glu Tyr Gly Leu Pro
                325                 330                 335

Glu Thr Gln Glu Leu Thr Ile Thr
                340
```